United States Patent
Chabanne et al.

(10) Patent No.: US 10,403,076 B2
(45) Date of Patent: Sep. 3, 2019

(54) METHOD FOR SECURING AND VERIFYING A DOCUMENT

(71) Applicant: Safran Identity & Security, Issy-les-Moulineaux (FR)

(72) Inventors: Herve Chabanne, Issy les Moulineaux (FR); Jean-Christophe Fondeur, Issy les Moulineaux (FR); Stephane Gentric, Issy les Moulineaux (FR); Erik Van Dijk, Issy les Moulineaux (FR)

(73) Assignee: SAFRAN IDENTITY & SECURITY, Issy les Moulineaux (FR)

( * ) Notice: Subject to any disclaimer, the term of this patent is extended or adjusted under 35 U.S.C. 154(b) by 96 days.

(21) Appl. No.: 15/429,093

(22) Filed: Feb. 9, 2017

(65) Prior Publication Data

US 2017/0236355 A1    Aug. 17, 2017

(30) Foreign Application Priority Data

Feb. 11, 2016    (FR) ...................................... 16 51105

(51) Int. Cl.
    *G07D 7/00*    (2016.01)
    *G07D 7/20*    (2016.01)
    (Continued)

(52) U.S. Cl.
    CPC ........... *G07D 7/2016* (2013.01); *G01N 21/00* (2013.01); *G07D 7/003* (2017.05); *G07D 7/004* (2013.01);
    (Continued)

(58) Field of Classification Search
    CPC ...... G07D 7/205; G07D 7/124; G07D 7/2016; G07D 7/01; G07D 7/004; G07D 7/0047;
    (Continued)

(56) References Cited

U.S. PATENT DOCUMENTS

| | | | | |
|---|---|---|---|---|
| 2006/0015733 A1* | 1/2006 | O'Malley | ............... | G07D 7/004 713/176 |
| 2008/0149713 A1* | 6/2008 | Brundage | ............. | G06T 1/0071 235/435 |

(Continued)

FOREIGN PATENT DOCUMENTS

| EP | 1139302 A1 | 10/2001 |
|---|---|---|
| EP | 2290619 A1 | 3/2011 |

OTHER PUBLICATIONS

Search Report in French Application No. 1651105 dated Dec. 8, 2016, with English translation coversheet. 3 pages.

(Continued)

*Primary Examiner* — Ali Bayat
(74) *Attorney, Agent, or Firm* — Womble Bond Dickinson (US) LLP

(57) ABSTRACT

The invention relates to a method for securing a document including a visual element, carried out by a processing unit comprising processing means, the method comprising generation, from the visual element, of a reference security datum, and storage of the reference security datum, wherein the reference security datum is generated by means of an algorithm configured so as to generate:

for any image acquired from the visual element, a security datum whereof the differences relative to the reference security datum are less than a determined threshold, and for any image acquired on a different visual element, a security datum whereof the differences relative to the reference security datum are greater than said threshold.

18 Claims, 2 Drawing Sheets

(51) Int. Cl.
*G07D 7/004* (2016.01)
*G07D 7/0047* (2016.01)
*G07D 7/01* (2016.01)
*G01N 21/00* (2006.01)
*G07D 7/005* (2016.01)
*G07D 7/202* (2016.01)

(52) U.S. Cl.
CPC ............ *G07D 7/005* (2017.05); *G07D 7/0032* (2017.05); *G07D 7/0034* (2017.05); *G07D 7/0047* (2017.05); *G07D 7/0053* (2013.01); *G07D 7/01* (2017.05); *G07D 7/205* (2013.01); *G07D 7/2083* (2013.01)

(58) Field of Classification Search
CPC .... G07D 7/0013; G07D 7/002; G07D 7/0033; G07D 7/0046; G07D 7/0053; G07D 7/2083; G01N 21/00
USPC .......................................................... 382/159
See application file for complete search history.

(56) References Cited

U.S. PATENT DOCUMENTS

| | | | |
|---|---|---|---|
| 2008/0294900 A1 | 11/2008 | Cowburn | |
| 2010/0185864 A1* | 7/2010 | Gerdes, Jr. | H04L 9/3213 |
| | | | 713/175 |
| 2013/0173484 A1* | 7/2013 | Wesby | G06Q 30/06 |
| | | | 705/318 |
| 2018/0165781 A1* | 6/2018 | Rodriguez | G06K 7/10297 |
| 2018/0181964 A1* | 6/2018 | Zagarese | G06Q 20/40145 |

OTHER PUBLICATIONS

Written Opinion in French Application No. 1651105 dated Dec. 15, 2016, with English translation coversheet. 6 pages.

* cited by examiner

METHOD FOR SECURING AND VERIFYING A DOCUMENT

FIELD OF THE INVENTION

The invention relates to the field of securing documents comprising at least one visual element. Documents can be especially identity documents for example of identity card, driving license, birth certificate or passport type or else any "electronic document" (documents of personal and/or identity type) which can be hosted on a smartphone or other portable device having display means. The invention also relates to verification of the integrity of such documents once secured.

PRIOR ART

National security services have discovered frauds perpetrated using identity documents, wherein an authentic document provided with an original identity photograph has been falsified, by replacing the photograph by the photograph of a different person. Due to this the user of the falsified document can usurp the identity of the person to whom the identity document was initially issued.

In a more general context, demands imposed in terms of security to organizations designing and issuing identity documents are becoming stricter.

PRESENTATION OF THE INVENTION

An aim of the invention is to propose a method for securing a document, especially an identity document, ensuring especially the integrity of visual elements of the document such as photographs.

Another aim of the invention is to propose a method for verifying the integrity of a document secured by the proposed method.

Another aim of the invention is to ensure that the method for verifying the integrity of the document is robust to variations undergone by the document linked to its use, its conditions of use, etc.

In this respect, the object of the invention is a method for securing a document including a visual element, carried out by a processing unit comprising processing means, the method comprising generation, from the visual element, of a reference security datum, and storage of the reference security datum,
wherein the reference security datum is generated by means of an algorithm configured so as to generate:
  for any image acquired from the visual element, a security datum whereof the differences relative to the reference security datum are less than a determined threshold, and
  for any image acquired on a different visual element, a security datum whereof the differences relative to the reference security datum are greater than said threshold.

Preferably, the algorithm is parameterized from training on a learning database. Advantageously, but optionally, the method according to the invention can further comprise at least one of the following characteristics:
  generation of the reference security datum is carried out during the creation of the document.
  the reference security datum is stored in the document, by recording of the datum in an electronic chip stored in the document or display, for example printing, of the datum on the document.
  the reference security datum is stored by being recorded in a database.
  the reference security datum is signed by the processing unit, by means of a signature algorithm with public key, or recorded with a certificate of authenticity obtained by application of a coding algorithm based on use of an error-correction code, so-called secure sketch.
  the reference security datum is stored in the document by display, for example printing, of the datum on the document and the visual element is also displayed, for example printed, on the document.
  the document is an electronic document comprising display means, for example a screen.
  the algorithm is selected such that reconstitution of the visual element from the corresponding security datum is impossible.
  the algorithm is a descriptor algorithm of BRIEF type, or of SIFT type, or of SURF type or of GLOH type, or of ORB type, or of BRISK type or of FREAK type or of LATCH type.
  the algorithm is of the type comprising the use of histograms of gradients oriented on the visual element, or of convolutional neural networks, or again of BRIEF type, or of SIFT type, or of SURF type or of GLOH type, or of ORB type, or of BRISK type or of FREAK type or of LATCH type.
  for training the algorithm, the algorithm is executed
    on a large number of pairs of images, and indications are provided on those which must result in substantially identical security data, (typically the same image captured at instants and/or in different conditions, for example when the image has deteriorated over time, friction, yellowing and/or during acquisition, luminosity, angle, etc. are not the same), and
    on other pairs of images which must result in substantially different security data, (typically when the pair comprises two different images or different individuals, or the same individual, for example in the event where the other image has been taken at different times and/or under different conditions).
  the visual element is an image of the face of an individual, and the algorithm is trained so as to generate:
    for any image acquired from the image of the face of the individual featured on the document, a security datum whereof the differences relative to the reference security datum are less than a determined threshold, and
    for any image acquired from an image representing another individual, or the same individual in different image acquisition conditions, a security datum whereof the differences relative to the reference security datum are greater than said threshold.

Another object of the invention is a method for securing a document including a visual element, carried out by a processing unit comprising processing means, the method comprising generation, from the visual element, of a reference security datum, and storage of the reference security datum,
wherein the reference security datum is generated by means of an algorithm parameterized from training on a learning database,
wherein, for training the algorithm, the algorithm is executed
  on a large number of pairs of images, and indications are provided on those which must result in substantially identical security data, on other pairs of images which must result in substantially different security data.

In particular, the algorithm is preferably configured so as to generate:

for any image acquired from the visual element, a security datum whereof the differences relative to the reference security datum are less than a determined threshold, and for any image acquired on a different visual element, a security datum whereof the differences relative to the reference security datum are greater than said threshold.

The additional characteristics described previously apply also for this object.

Another object of the invention is a computer program product, comprising code instructions for carrying out a method according to the foregoing description, when it is executed by processing means of a processing unit.

Another object of the invention is a secure document which can be obtained by carrying out a method according to the foregoing description.

Another object of the invention is a method for verifying the integrity of a document secured by carrying out the method according to the foregoing description, the method comprising the steps of:

acquiring an image of the visual element of the document, generating, from the image, a security datum by the same algorithm as that having generated the reference security datum, comparing the security datum obtained to the reference security datum, and if the differences between the security datum and the reference security datum are less than the determined threshold, determining that the visual element is integral, if not determining that the visual element is fraudulent.

Advantageously, but optionally, the verification method further comprises, prior to the comparison step, a verification step of the integrity of the reference security datum.

A final object of the invention is a system for verifying a document, comprising:

an image sensor, a processing unit, comprising processing means adapted to carry out, on an image acquired by the sensor, a classification algorithm, and a communications interface with a database, the verification system being configured to carry out the verification method according to the foregoing description.

The proposed method ensures the integrity of a visual element of a document such as a photograph, or again a chain of characters, a signature, etc. In fact, attributed to each visual element is a reference security datum which is obtained by an algorithm configured so that the datum obtained is overall the same for all images of a same visual element, irrespective of the conditions of acquisition of the images or the wear of the element, and which is different for images of a different visual element.

For this, the algorithm is trained on a learning database.

To further reinforce the security of the document, the integrity of the reference security datum can be guaranteed by means of a signature algorithm with public key or a coding algorithm called secure sketch. In this way, the security datum cannot be falsified by the individual carrying the document.

DESCRIPTION OF THE FIGURES

Other characteristics, aims and advantages of the present invention will emerge from the following detailed description, with respect to the appended figures, given by way of non-limiting examples and in which.

DETAILED DESCRIPTION OF AT LEAST ONE EMBODIMENT OF THE INVENTION

Securing a Document

Figure 1A:
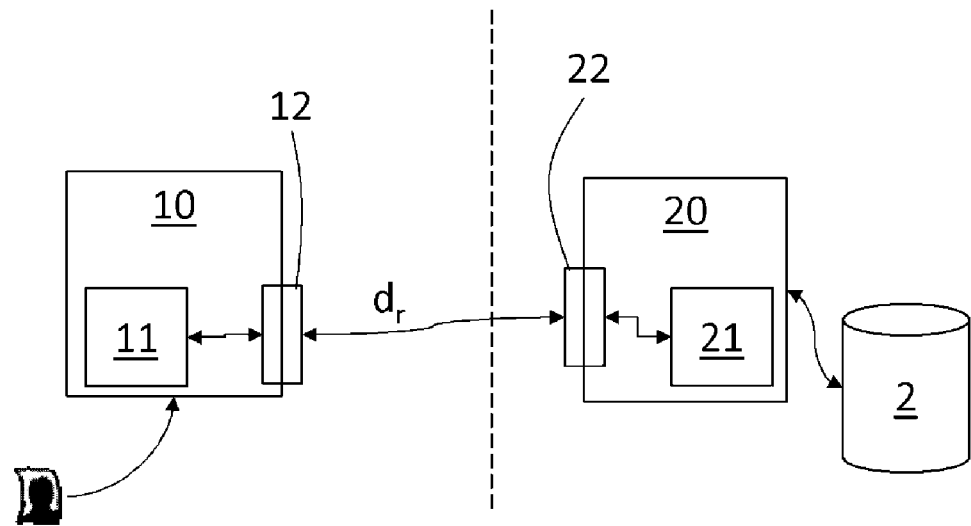
FIGS. 1a and 1b schematically illustrate a processing system for securing a document and a system for verifying the integrity of a document.

In reference to FIG. 1a, this shows a processing system for securing a document, for example an identity document such as a passport, an identity card, etc. The type of document is not limited to an identity document, but could also relate to documents for playing, for example a personal smart card for playing at the casino, etc. The document can be any "electronic document" (personal and/or identity documents type) which can be hosted on a smartphone or other portable devices, and comprising display means, for example a screen.

This system comprises a processing unit 10, for example a computer or a server, having processing means 11 adapted to carry out an algorithm to be described in more detail hereinbelow. The processing means 11 can for example be a calculator of type processor, microprocessor, microcontroller, etc.

The processing unit 10 can also be adapted to carry out cryptographic algorithms, for example of signature algorithm type with public key or of "secure sketch" type mentioned in more detail hereinbelow.

The processing unit 10 and the processing means 11 are operated by an entity considered non-fraudulent, typically a government in the event where the document is an identity document.

Advantageously, the system can also comprise a database 2, and a processing unit 20 managing the database. The processing unit can also be a computer or a server, having processing means 21, for example a calculator of type processor, microprocessor, microcontroller, etc., letting the processing unit access the database for reading and writing.

The two processing units 10, 20 advantageously comprise remote communication interfaces 12, 22 for sending and receiving data, for example via wireless Internet, radiofrequency signal, etc.

Figure 2:
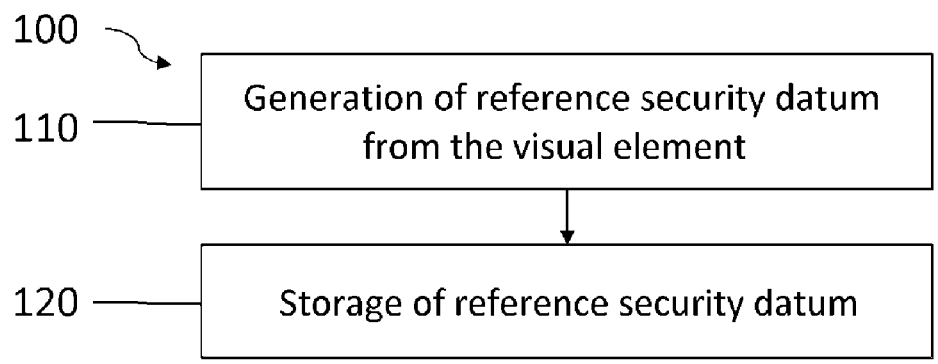
FIG. 2 schematically illustrates the main steps of a method for securing a document, FIG. 3 schematically illustrates the main steps of a method for verifying the integrity of a document.

In reference to FIG. 2, a method 100 for securing a document comprises a visual element featured on the document.

This visual element is an image comprising pertinent data during use of the document. In the case of an identity document, the visual element is an image comprising data linked to the individual to whom the identity document is issued. Advantageously, this is an identity photograph, i.e., a photograph representing a distinctive sign of the individual to whom the document has been issued, typically its face. Alternatively, the visual element can also be an image of a distinctive sign of the individual, for example a handwritten signature.

The visual element can also be the representation on the document of a set of signs linked to the identity of the individual, for example a chain of characters (name, first name, date of birth, etc.).

According to another variant, the visual element can be the entire document, for example in the event where the document used is electronic and is displayed on a screen of an electronic device such as a tablet or a mobile telephone.

Securing the visual element is preferably carried out during creation of the document, to ensure that the visual element is authentic.

Securing of the visual element comprises generation 110, by the processing unit 10, from the visual element, of a security datum, called reference datum $d_r$. This datum advantageously takes the form of a sequence of bits, of a length from a few octets to a few tens of octets.

If the visual element is a digital image inserted in the document during its manufacture, step 110 is carried out directly on the element. Alternatively, step 110 can be carried out on an image of the visual element captured on the document by means of an appropriate digital image sensor (not shown).

The visual element can be processed before the reference security datum is generated. It can be advantageously reset relative to a referential, either by alignment, or by attempting to have particular points correspond, for example by using the SIFT method. Then the visual element can be standardized for example by the histogram equalization method.

The reference security datum $d_r$ is obtained from the visual element by carrying out an algorithm which is configured to obtain properties preferred for the reference security datum.

A first property is the following:

Images acquired from a same visual element, irrespective of the conditions of acquisition, must result in obtaining substantially identical security data via the algorithm.

Hereinbelow, "substantially identical security data" mean security data having between them differences less than a determined threshold. The number of differences between two security data can be evaluated as is known by using a metric adapted for example by calculating a distance between the data, such as for example Euclidian distance or Hamming distance. The value of the threshold depends on the nature of the function calculated.

The acquisition conditions of the image of the visual element combine overall:

uncertainties linked to the conditions of the acquisition itself with an image sensor, for example the lighting conditions, the parameters of the image sensor, the distance from the visual element relative to the sensor, etc., and:

uncertainties linked to the appearance of the visual element, such as for example a variation in appearance of the document originating from its ageing, yellowing of a photograph, the appearance of scratches or marks, or even a variation in appearance linked to additions made to heighten security of the document: presence on a part of the element of a buffer, a hologram, etc.

In particular, a security datum obtained from an image of the same visual element as that from which the reference security datum is obtained must be substantially identical to the latter.

Another property is the following:

Images acquired of different visual elements must result in obtaining, via the algorithm, substantially different security data.

Hereinbelow, "substantially different security data" mean security data having between them differences greater than the threshold previously mentioned.

In particular, a security datum obtained from an image of a visual element different to that from which the reference security datum $d_r$ is obtained, must be substantially different to the reference security datum.

Also, in the event where the visual element of the document is a photograph of an individual, the security datum must be substantially the same as the reference security datum $d_r$ (i.e., exhibit differences less than a certain threshold) for all images taken of the same photograph of the same individual.

However, a security datum must be substantially different to the reference security datum $d_r$ if it is obtained from any other photograph of the same individual, or any photograph of another individual.

To obtain these properties, the algorithm is trained, i.e., parameterized on a learning database (not shown) containing a set of images. During this training, the algorithm is executed on a large number of pairs of images, and indications are provided on those which must result in substantially identical security data (typically the same image captured at instants and/or in different conditions, for example when the image has deteriorated over time, friction, yellowing and/or during acquisition, luminosity, angle, etc. are not the same), and on other pairs of images which must result in substantially different security data (typically when the pair comprises two different images of a same object or different objects but of the same kind, more particularly when the pair includes two different images either of different individuals (or other objects), or of a same individual (or object), for example in the event where the other image has been taken at different moments and/or in different conditions).

The value of the threshold setting a classification between substantially identical data and substantially different data is determined by the algorithm on completion of its learning.

Advantageously, the learning database comprises the most images possible, for example at least 10,000 images, and preferably at least one million, as the more the database comprises images the more the learning on this database boosts the reliability of the algorithm.

The classification algorithm selected to generate the security datum from an image is advantageously a classification algorithm of the type employing a convolutional neural network also known by the acronym CNN.

As is known to the skilled person, a convolutional neural network includes a structure formed by a succession of operations carried out on an input datum (in this case an image), the operations comprising linear operations of convolution type, whereof the result is weighted by a weighting factor, and non-linear operations, for example thresholding, etc.

The adjustment of the algorithm during learning amounts to adjusting the values of the weighting factors.

An example of a structure of a convolutional neural network applicable to generation of a security datum from an image is that which is detailed for the network F1 of the document by Y. Sun et al., "*Deep Convolutional Network Cascade for Facial Point Detection*", Proceedings of IEEE Conference on Computer Vision and Pattern Recognition (CVPR), 2013.

The learning mode of parameters of the CNN algorithm, such that it generates two different security data from different images of a same person, and the presence of non-linear operations in the generation of the datum from the visual element, prevents reconstitution of the image from the security datum and preserves confidentiality of data contained in the image on the individual.

Alternatively, the algorithm can be of the BRIEF type (for "Binary Robust Independent Elementary Feature"), such as described in the eponymous publication by Fua et al. ("Brief: Binary Robust Independent Elementary Features"; Calonder, Lepetit, Strecha, Fua; CvLab, EPFL). However, inversely to this publication where the BRIEF algorithm is used is extract characteristics ("features") from images, the algorithm is here used to detect alterations to the visual element. So, in place of BRIEF weighting ("weight factors"), a learning step ("machine learning") is used to generate the most adequate pattern of point pair ("point pair pattern"), founded on a minimal Hamming distance between the original visual element, typically the photograph of the face, and the visual element of the document (the original which has undergone alterations), and on a major Hamming distance between the original visual element and a fraudulent visual element. The pattern is generated by selection from a large number of pairs of points drawn randomly.

Alternatively, another binary descriptor of type SIFT, SURF, GLOH, ORB, BRISK, FREAK, LATCH . . . , or same a descriptor of HOG type can be used (see hereinbelow). These descriptors have been introduced to capture characteristic elements of images. Here they are constructed to also satisfy the foregoing properties: allowing recognition of the same image and preventing reconstruction of the visual element from a corresponding security datum.

Alternatively, the algorithm can be of the type employing a HOG descriptor, i.e., with a histogram of oriented gradient.

Such an algorithm is applied to an image distributed in areas. For each area, gradients are calculated for a set of points of the area, independently of their position in the area, and a histogram of directions of gradients is aggregated for all the gradients calculated on the area.

The algorithm then comprises concatenation of the set of histograms of gradients oriented for all the areas, and reduction of the vector obtained by a method of space reduction of a type for example of analysis in main components or linear discriminating analysis.

This algorithm can also comprise a preliminary processing step of images for standardizing the colors of images and the contrast factor.

Reference could be made to the publication by N. Dalai et al., "*Histograms of Oriented Gradients for Human Detection*", *Conference on Computer Vision and Pattern Recognition*, 2005, for more details and an example of implementation of an algorithm based on a HOG descriptor.

In this embodiment, parameterization of the algorithm on the learning database to satisfy the two properties detailed hereinabove on the conditions of similarity and dissimilarity of security data, comprises adjustment of parameters linked to pre-processing, the size of selected areas, the number of gradients per area, the type of filters used to calculate the gradients, the kind of selected space reduction, etc.

The use of such an algorithm, which eliminates location of information on the image, also ensures confidentiality of visual elements and prevents reconstituting a visual element from a corresponding security datum.

Preferably, in the case of a visual element comprising biometric information (such as a photograph), the above algorithms do not seek to recognize the person present on the visual element, as is often preferred in biometric identification, but only to know if the visual element is authentic. Consequently, this means that their execution does not involve identification of the person possessing the document. This is why a document comprising another visual element representing the person present on the visual reference element (typically another photograph representing the same person as that present on the reference photograph) will be considered as fraudulent after verification, while it would result in authentication or biometric identification.

Once the reference security datum $d_r$ is obtained for the visual element of the document, this datum is stored during a step 120.

It can be stored in the document itself. For example, it can be stored in memory in an electronic chip integrated into the document.

Alternatively, it can be printed on the document, visibly or not, i.e., for example as a watermark, in the form of a barcode, etc.

Alternatively, it can be stuck on, deposited or etched onto the document, so that there is a physical display.

In the two foregoing alternatives, the reference datum can be visible or invisible (as for known "digital watermark").

More generally, this is display.

But the reference security datum $d_r$ is preferably stored in a database 2 managed by a manager processing unit 20 which can be reliable, for example dependent on a State agency. This limits access possibilities, by a malevolent individual or by the holder of the document himself to the datum stored in the document.

In this case, the processing unit 10 communicates the reference security datum to the processing unit 20 which stores it in the base. This communication can be carried out over a secure channel and/or by means of a cryptographic protocol to ensure confidentiality of the datum.

Also, and irrespective of the storage medium of the security datum, the integrity of this security datum is itself preferably guaranteed.

For example, the security datum can be signed by the processing unit 10 which has generated the security datum, for example by means of a signature algorithm with public key, conventionally using a private key which is detained by the unit 20, and a public key.

As a variant, the integrity of the security datum can be ensured by means of an algorithm of secure sketch type, i.e., a coding algorithm based on use of an error-correction code, which comprises execution, by the processing unit 10, of the steps of:

Binarizing if needed the security datum to produce a datum b,

From a word c of an error-correction code, obtaining from the reference a result such as $r=[c\ XOR\ b, h(c)]$, where XOR is the function "exclusive or", and h is a function of cryptographic hashing, for example of SHA-256 type, and record the result r with the security datum, either in the document or in the database 2.

Verification of the Integrity of a Document

Figure 1B:
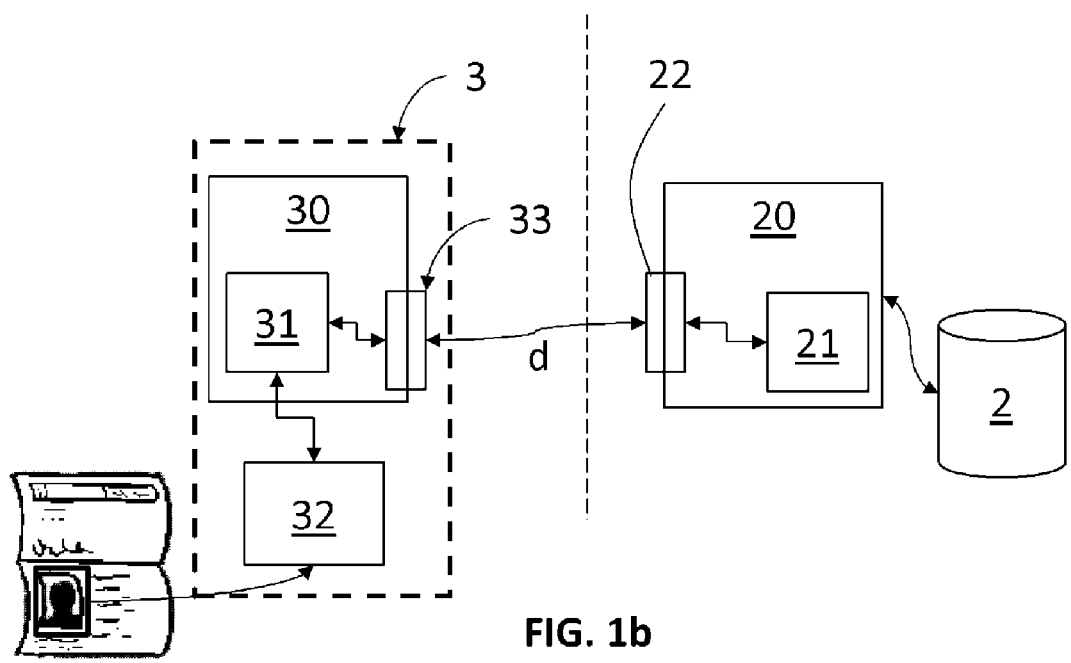

In reference to FIG. 1b, this shows a verification system 3 of the integrity of a document. Verification can take place for example during a check of the document, or check of the identity of an individual in the event where the document is an identity document of the individual.

The verification system 3 advantageously comprises a processing unit 30, comprising processing means 31 such as a computer, for example of type processor, microprocessor, microcontroller, etc.

The processing means 31 are adapted to carry out an algorithm identical to that which has already been described hereinabove to obtain a security datum from an image.

The verification system also comprises an image sensor 32, typically a digital photographic device. It can be a photographic device integrated into a mobile telephone (smartphone) or a digital tablet.

The verification system 3 is advantageously integrated into a carry case so it can be deployed easily during a control; for example the verification system can be integrated into a mobile telephone, a digital tablet, etc.

If needed, if the reference security datum is recorded in the database 2, the verification system 3 finally comprises a communications interface 33 adapted to remote-communicate with the manager processing unit 20 of the database 2, for example via wireless Internet, radiofrequency signal, etc.

Figure 3:
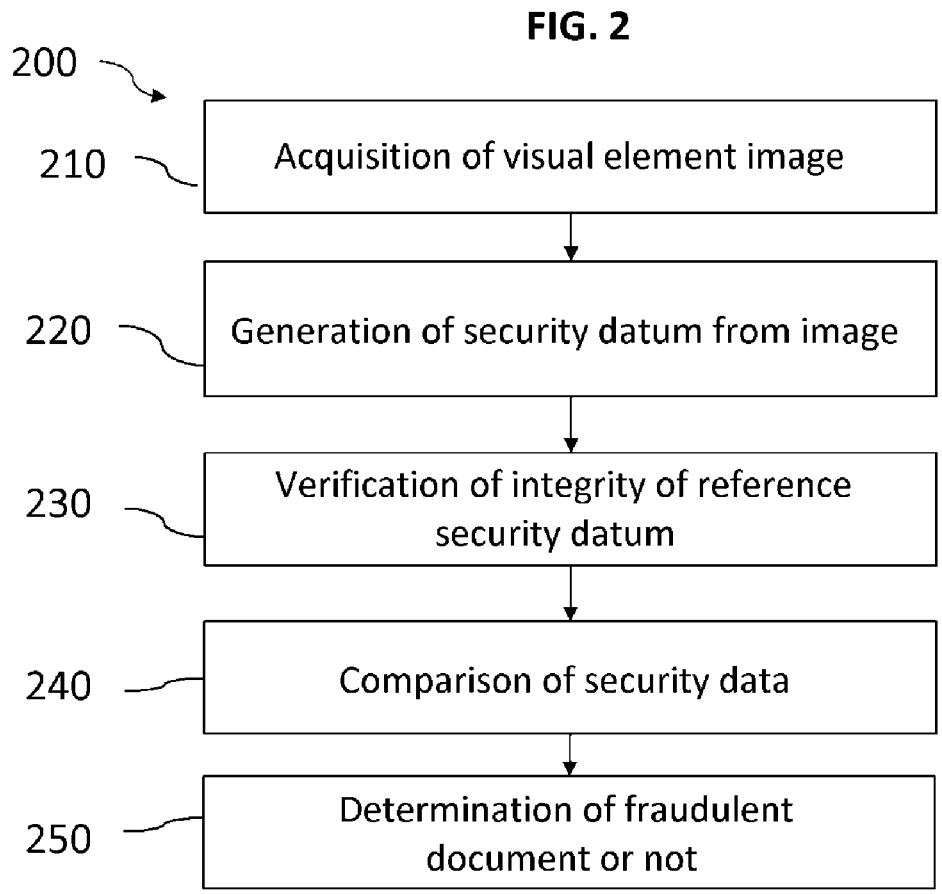

In reference to FIG. 3, a verification method 200 of the integrity of a document comprises a first acquisition step 210, with the image sensors 32, of an image of the visual element of the document the integrity of which is to be verified.

Then, the processing unit 30 executes 220, from this image, the same algorithm as that which has been executed during the method for securing to obtain the reference security datum $d_r$, and it obtains a new security datum d.

Advantageously, the image acquired during step 210 can be processed in the same way as for the visual element prior to generating the new security datum to blur the variations linked to taking the image. In this way the image can also be reset and standardized.

The processing unit 30 then recovers, from the database 2 or the document, the reference security datum $d_r$ corresponding to the visual element to be verified.

Advantageously, the verification method 200 comprises a verification step 230 of the integrity of the reference security datum.

If the reference security datum $d_r$ has been signed by the processing unit 10, the processing unit 30 of the verification system 3 verifies during a step 230 that the signature is valid by using the public key associated with the private key used during signing.

If the reference security datum is recorded with a result r of the application of a secure sketch algorithm, the integrity of the reference datum is verified during a same step 230 by the processing unit 30. For this to happen, the processing unit 30 binarizes the new security datum d to obtain a binarized datum b'.

It then calculates c XOR b XOR b' from the datum r. If b and b' are sufficiently close then this operation provides the code word c used initially by the unit 10, because of the corrective capacity of the corrective code and therefore ensures the integrity of the reference security datum.

If the result of verification step 230 indicates that the reference security datum is not integral, the processing unit 30 determines that the document is fraudulent.

If the result of verification step 230 indicates that the reference security datum is integral, the processing unit 30 compares during a step 240 the new security datum d to the reference security datum $d_r$, by calculation between these data of an appropriate function such as a Euclidian distance, a Hamming distance, etc, and compares the result to a determined threshold, which corresponds to the threshold introduced hereinabove, and discriminating substantially identical images and substantially different images.

The method 200 finally comprises a determination step 250, as a function of the result of the comparison, of the fraudulent character or not of the document. If the differences between the two data are less than the threshold, the document is considered integral. If not, the document is considered falsified.

The invention claimed is:

1. A method for securing a document including a visual element, carried out by a processing unit comprising processing means, the method comprising
   generation, from the visual element, of a reference security datum, and
   storage of the reference security datum,
   wherein the reference security datum is generated by processing means of an algorithm parameterized from training on a learning database,
   wherein, for training the algorithm, the algorithm is executed
      on a large number of pairs of images, and indications are provided on those which must result in substantially identical security data,
      on other pairs of images which must result in substantially different security data.

2. The method for securing a document according to claim 1, wherein generation of the reference security datum is carried out during creation of the document.

3. The method for securing a document according to claim 1, wherein the reference security datum is stored in the document, by display, for example printing, of the datum on the document or by recording of the datum in an electronic chip stored in the document.

4. The method for securing a document according to claim 3, wherein the reference security datum is signed by the processing unit, by processing means of a signature algorithm with public key, or recorded with a certificate of authenticity obtained by application of a coding algorithm based on use of an error-correction code, so-called secure sketch.

5. The method for securing a document according to claim 1, wherein the reference security datum is stored by being recorded in a database.

6. The method for securing a document according to claim 1, wherein the reference security datum is stored in the document by display, for example printing, of the datum on the document and wherein the visual element is also displayed, for example printed, on the document.

7. The method for securing a document according to claim 1, wherein the document is an electronic document preferably comprising display means.

8. The method for securing a document according to claim 1, wherein the algorithm is selected such that reconstitution of the visual element from the corresponding security datum is impossible.

9. The method for securing a document according to claim 1, wherein the algorithm is of the type comprising the use of histograms of gradients oriented on the visual element, or of convolutional neural networks, or of descriptor algorithm type.

10. The method for securing a document according to claim 1, wherein the algorithm is a descriptor algorithm of BRIEF type, or
    of SIFT type, or of SURF type or of GLOH type, or of ORB type, or of BRISK type or
    of FREAK type or of LATCH type.

11. The method for securing a document according to claim 1, wherein said algorithm being trained so as to generate:
    for any image acquired from the visual element, a security datum whereof the differences relative to the reference security datum are less than a determined threshold, and
    for any image acquired on a different visual element, a security datum whereof the differences relative to the reference security datum are greater than said threshold.

12. A computer program product stored on a non-transitory medium, comprising code instructions for carrying out a method according to claim 1, when it is executed by processing means of a processing unit.

13. A secure document which can be obtained by carrying out a method according to claim 1.

14. The method for securing a document according to claim 1, wherein the visual element is an image of the face of an individual, and the algorithm is trained so as to generate:
- for any image acquired from the image of the face of the individual featured on the document, a security datum whereof the differences relative to the reference security datum are less than a determined threshold, and
- for any image acquired from an image representing another individual, or the same individual in different image acquisition conditions, a security datum whereof the differences relative to the reference security datum are greater than said threshold.

15. The method for securing a document including a visual element, carried out by a processing unit comprising processing means, the method
- comprising generation, from the visual element, of a reference security datum, and storage of the reference security datum,
- wherein the reference security datum is generated by processing means of an algorithm parameterized from training on a learning database, said algorithm being trained so as to generate:
  - for any image acquired from the visual element, a security datum whereof the differences relative to the reference security datum are less than a determined threshold, and
  - for any image acquired on a different visual element, a security datum whereof the differences relative to the reference security datum are greater than said threshold.

16. A method for verifying the integrity of a document secured by carrying out the method according to claim 1, the method comprising the steps of:
- acquiring an image of the visual element of the document,
- generating, from the image, a security datum by the same algorithm as that having generated the reference security datum,
- comparing the security datum obtained to the reference security datum, and
- if the differences between the security datum and the reference security datum are less than the determined threshold, determining that the visual element is integral, if not determining that the visual element is fraudulent.

17. The verification method according to claim 16, wherein the method further comprises, prior to the comparison step, a verification step of the integrity of the reference security datum.

18. A system for verifying a document, comprising:
- an image sensor,
- a processing unit, comprising processing means adapted to carry out, on an image acquired by the sensor, a classification algorithm, and a communications interface with a database, the verification system being configured to carry out the method according to claim 16.

* * * * *